United States Patent
Igarashi et al.

(10) Patent No.: US 11,350,824 B2
(45) Date of Patent: Jun. 7, 2022

(54) MEDICAL IMAGE DIAGNOSIS APPARATUS AND MEDICAL IMAGE DIAGNOSIS SYSTEM

(71) Applicant: Canon Medical Systems Corporation, Otawara (JP)

(72) Inventors: Takuma Igarashi, Nasushiobara (JP); Qiqi Xu, Beijing (CN); Fanjie Meng, Beijing (CN)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 550 days.

(21) Appl. No.: 16/275,773

(22) Filed: Feb. 14, 2019

(65) Prior Publication Data

US 2020/0163550 A1    May 28, 2020

(30) Foreign Application Priority Data

Nov. 23, 2018    (CN) .......................... 201811405493.1

(51) Int. Cl.
   *A61B 5/05*    (2021.01)
   *A61B 5/00*    (2006.01)
   *A61B 5/055*   (2006.01)

(52) U.S. Cl.
   CPC ............ *A61B 5/0042* (2013.01); *A61B 5/055* (2013.01); *A61B 5/7246* (2013.01)

(58) Field of Classification Search
   CPC combination set(s) only.
   See application file for complete search history.

(56) References Cited

U.S. PATENT DOCUMENTS

| | | | |
|---|---|---|---|
| 8,190,232 B2 | 5/2012 | Zhang et al. | |
| 2004/0077952 A1 | 4/2004 | Rafter et al. | |
| 2005/0228696 A1* | 10/2005 | Egawa | G16H 40/20 705/2 |
| 2015/0208994 A1* | 7/2015 | Rapoport | A61B 6/5247 600/411 |

(Continued)

FOREIGN PATENT DOCUMENTS

| | | |
|---|---|---|
| JP | 2006-503620 | 2/2006 |
| JP | 2015-100681 | 6/2015 |

(Continued)

*Primary Examiner* — Joel F Brutus
(74) *Attorney, Agent, or Firm* — Oblon, McClelland, Maier & Neustadt, L.L.P.

(57) ABSTRACT

A medical image diagnosis apparatus according to an embodiment includes an imager, a storage, and processing circuitry. The storage stores therein a correspondence relationship between each of disease patterns and scans used for performing a differential diagnosis process on the disease pattern. The processing circuitry obtains, based on image data acquired by a first scan, a disease pattern having a possibility of being applicable to the subject and a first index value indicating a degree of applicability of the disease pattern. The processing circuitry outputs information indicating the disease pattern to a display when it is possible to perform the differential diagnosis process based on the first index value and outputs an imaging condition used for performing a second scan based on the correspondence relationship and the disease pattern having the possibility when it is not possible to perform the differential diagnosis process based on the first index value.

14 Claims, 5 Drawing Sheets

(56) References Cited

U.S. PATENT DOCUMENTS

2016/0048956 A1* 2/2016 Bryan .................. G06T 7/0012
382/128
2017/0323447 A1 11/2017 Tsukagoshi et al.

FOREIGN PATENT DOCUMENTS

| JP | 2015-531661 | 11/2015 |
| JP | 20017-202310 | 11/2017 |
| WO | WO 2014/043661 A2 | 3/2014 |

* cited by examiner

MEDICAL IMAGE DIAGNOSIS APPARATUS AND MEDICAL IMAGE DIAGNOSIS SYSTEM

CROSS-REFERENCE TO RELATED APPLICATIONS

This application is based upon and claims the benefit of priority from Chinese Patent Application No. 201811405493.1, filed on Nov. 23, 2018, the entire contents of which are incorporated herein by reference.

FIELD

Embodiments described herein relate generally to a medical image diagnosis apparatus and a medical image diagnosis system.

BACKGROUND

Conventionally, in differential diagnosis processes performed at hospitals and the like, a location in the subject's body that is suspicious or related to a diagnosis is determined through an interview with a medical doctor or the like, and subsequently, an imaging process is performed on the determined location. Further, after an analysis is performed on the basis of one or more images acquired from the imaging process, a diagnosis is made. Further, when it is not possible to make a diagnosis from the imaged location alone, another imaging method such as imaging another location is considered, and an i g process is performed again.

DETAILED DESCRIPTION

A medical image diagnosis apparatus according to an embodiment includes an imager, a storage, and processing circuitry. The imager is configured to image a subject by performing a first scan. The storage is configured to store therein a correspondence relationship between each of a plurality of disease patterns and a plurality of scans used for performing a differential diagnosis process on the disease pattern. The processing circuitry is configured to obtain, on the basis of first image data acquired from the first scan, a disease pattern having a possibility of being applicable to the and a first index value indicating a degree of applicability of the disease pattern. The processing circuitry is configured to output information indicating the disease pattern to a display when it is possible to perform the differential diagnosis process on the disease pattern on the basis of the first index value and to output an imaging condition used for causing the imager to image the subject by performing a second scan different from the first scan on the basis of the correspondence relationship and the disease pattern having the possibility of being applicable to the subject when it is not possible to perform the differential diagnosis process on the disease pattern on the basis of the first index value.

Exemplary embodiments of a medical image diagnosis apparatus and a medical image diagnosis system will be explained in detail below, with reference to the accompanying drawings.

First Embodiment

Figure 1:
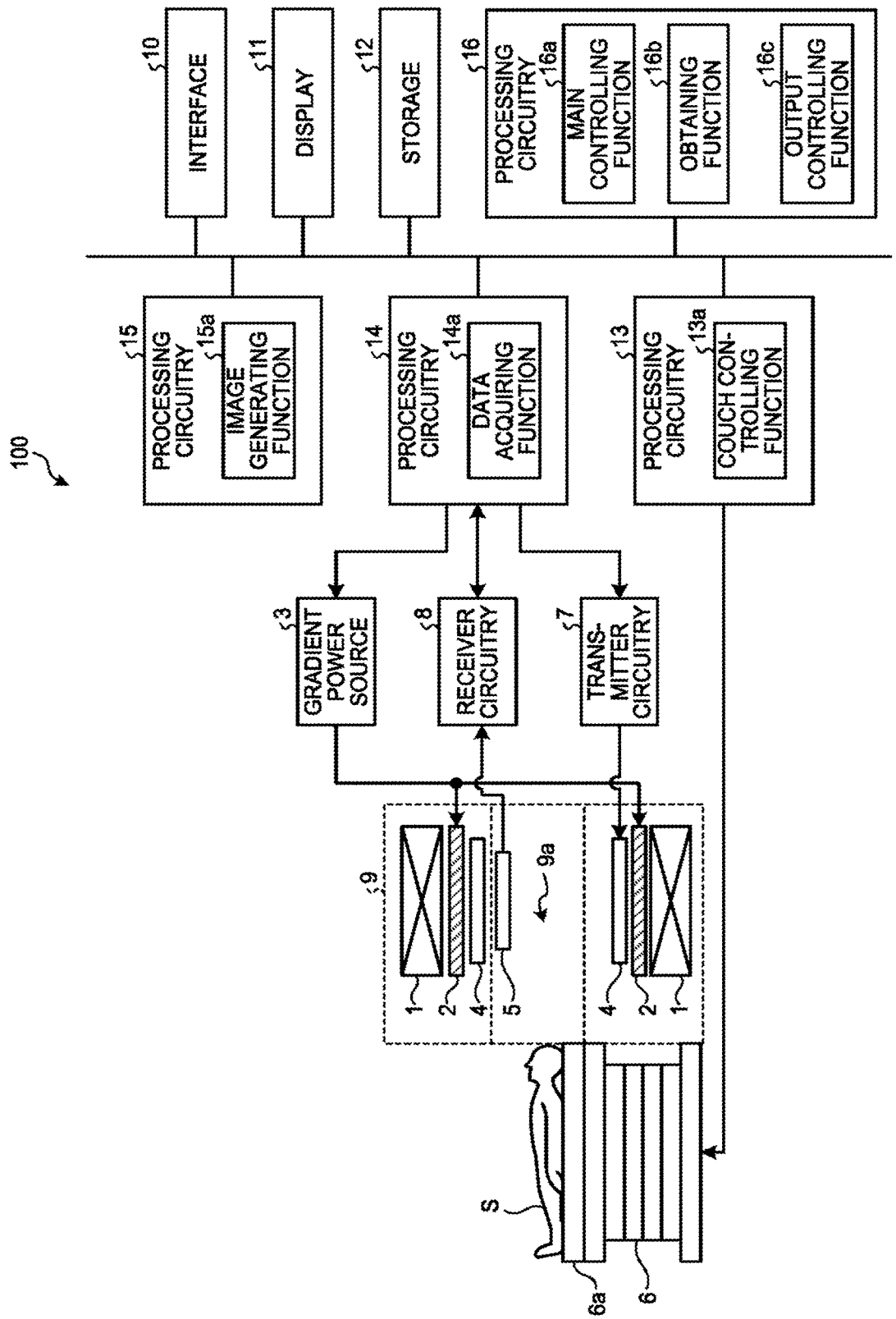
FIG. 1 is a diagram illustrating a configuration of a Magnetic Resonance Imaging (MRI) apparatus according to a first embodiment.

To begin with, as a first embodiment, an example will be explained in which a configuration of a medical image diagnosis apparatus of the present disclosure is applied to a Magnetic Resonance Imaging (MRI) apparatus FIG. 1 is a diagram illustrating an exemplary configuration of the MRI apparatus according to the first embodiment.

For example, as illustrated in FIG. 1, an MRI apparatus 100 according to the present embodiment includes a static magnetic field magnet 1, a gradient coil 2, a gradient power source 3, a whole body coil 4, a local coil 5, a couch 6, transmitter circuitry 7, receiver circuitry 0, a gantry 9, an interface 10, a display 11, a storage 12, and processing circuitries 13 to 16.

The static magnetic field magnet 1 is configured to generate a static magnetic field in an imaging space in which a subject is placed. More specifically, the static magnetic field magnet 1 is formed to have a hollow and substantially circular cylindrical shape (which may have an oval cross-section orthogonal to the central axis thereof) and is configured to generate the static magnetic field in the imaging space positioned on the inner circumferential side thereof. For example, the static magnetic field magnet 1 includes a cooling container formed to have a substantially circular cylindrical shape and a magnet such as a superconductive magnet that is immersed in a cooling member (e.g., liquid helium) filling the cooling container. In this situation, for example, the static magnetic field magnet 1 may be configured to generate the static magnetic field by using a permanent magnet.

The gradient coil 2 is configured to generate a gradient magnetic field in the imaging space in which the subject S is placed. More specifically, the gradient coil 2 is formed to have a hollow and substantially circular cylindrical shape (which may have an oval cross-section orthogonal to the central axis thereof) and includes a plurality of gradient coils being laminated in the radial direction and each having a substantially circular cylindrical shape. In this situation, the plurality of gradient coils are configured to generate gradient magnetic fields along axial directions of X-, Y-, and Z- axes that are orthogonal to one another, in the imaging space positioned on the inner circumferential side thereof, on the basis of an electric current supplied thereto from the gradient power source 3.

More specifically, as the gradient coils, the gradient coil 2 includes an X-coil configured to generate a gradient magnetic field along the X-axis direction, a Y-coil configured to generate a gradient magnetic field along the Y-axis direction, and a configured to generate a gradient magnetic field along the Z-axis direction. In this situation, the X-axis, the Y-axis, and the -axis structure an apparatus coordinate system unique to the MRI apparatus 100. For example, the X-axis is set so as to extend in a horizontal direction orthogonal to the central axis of the gradient coil 2. The Y-axis is set so as to extend in a vertical direction orthogonal to the central axis of the gradient coil 2. Further, the Z-axis is set so as to extend along the central axis of the gradient coil 2.

By individually supplying an electric current to each of the X-, Y-, and Z- coils included in the gradient coil 2, the gradient power source 3 is configured to cause the gradient magnetic fields to be generated along the axial directions of the X-, Y-, and Z- axes, in the imaging space. More specifically, by supplying the electric current to each of the X-, Y-, and Z- coils as appropriate, the gradient power source 3 causes the gradient magnetic fields to be generated along a readout direction, a phase encoding direction, and a slice direction, respectively, that are orthogonal to one another. In this situation, the axis extending along the readout direction, the axis extending along the phase encoding direction, and the axis extending along the slice direction structure a logical coordinate system used for defining slice regions or a volume region serving as a target of an imaging process.

Further, the gradient magnetic fields formed along the readout direction, the phase encoding direction, and the slice direction append spatial position information to MR signals emitted from the subject S, as a result of being superimposed on the static magnetic field generated by the static magnetic field magnet 1. More specifically, the gradient magnetic field in the readout direction appends position information along the readout direction to an MR signal, by varying the frequency of the MR signal in accordance with the position in the readout direction. Further, the gradient magnetic field in the phase encoding direction appends position information along the phase encoding direction to an MR signal, by varying the phase of the MR signal along the phase encoding direction. Further, the gradient magnetic field in the slice direction appends position information along the slice direction to an MR signal. For example, when an imaging region is represented by slice regions, the gradient magnetic field in the slice direction is used for determining the orientations, the thicknesses, and the quantity of the slice regions. In contrast, when an imaging region is represented by a volume region, the gradient magnetic field in the slice direction is used for varying the phase of the MR signal in accordance with the position in the slice direction.

The whole body coil 4 is a Radio Frequency (RF) coil configured to apply a Radio Frequency (RF) magnetic field to the imaging space in which the subject S is placed and to receive the MR signals emitted from the subject S due to an influence of the RF magnetic field. More specifically, the whole body coil 4 is formed to have a hollow and substantially circular cylindrical shape (which may have an oval cross-section orthogonal to the central axis thereof) and is configured to apply the RF magnetic field to the imaging space positioned on the inner circumferential side thereof, on the basis of an RF pulse signal supplied thereto from the transmitter circuitry 7. Further, the whole body coil 4 is configured to receive the MR signals emitted from the subject S due to the influence of the RF magnetic field and to output the received MR signals to the receiver circuitry 8. For example, the whole body coil 4 may be a quadrature (QD) coil of a birdcage type.

The local coil 5 is an RF coil configured to receive the MR signals emitted from the subject S. More specifically, the local coil 5 is an RF coil prepared for any of various sites of the subject S and is disposed in the vicinity of site subject to an imaging process, when the imaging process is to be performed on the subject S. Further, the local coil 5 is configured to receive the MR signals emitted from the subject S due to the influence of the RF magnetic field applied by the whole body coil 4 and to output the received MR signals to the receiver circuitry 8. The local coil 5 may further have a function of a transmission coil configured to apply an RF magnetic field to the subject S. In that situation, the local coil 5 is connected to the transmitter circuitry 7 and is configured to apply the RF magnetic field to the subject S on the basis of an RF pulse signal supplied thereto from the transmitter circuitry 7. For example, the local coil 5 may be a surface coil or may be an array coil structured with a plurality of surface coils.

The couch 6 includes a couchtop 6a on which the subject S is placed. When an imaging process is performed on the subject S, the couchtop 6a on which the subject S is placed is moved into the imaging space. For example, the couch 6 is installed in such a manner that the longitudinal direction of the couchtop 6a extends parallel to the central axis of the static magnetic field magnet 1.

The transmitter circuitry 7 is configured to output the RF pulse signal corresponding to a resonant frequency (a Larmor frequency) unique to a target atomic nucleus placed in the static magnetic field, to the whole body coil 4. More specifically, the transmitter circuitry 7 includes a pulse generator, an RF generator, a modulator, and an amplifier. The pulse generator is configured to generate a waveform of the RF pulse signal. The RF generator is configured to generate an RF signal having the resonant frequency. The modulator is configured to generate the RF pulse signal by modulating the amplitude of the RF signal generated by the RF generator, with the waveform generated by the pulse generator. The amplifier is configured to amplify the RF pulse signal generated by the modulator and to output the amplified RF pulse signal to the whole body coil 4.

The receiver circuitry 4 is configured to generate MR signal data on the basis of the MR signals received by either the whole body coil 4 or the local coil 5 and to output the generated MR signal data to the processing circuitry 14. More specifically, the receiver circuitry F includes a pre-amplifier, a signal detector, and an Analog/Digital (A/D) converter. The pre-amplifier is configured to amplify the MR signals output from either the whole body coil 4 or the local coil 5. The signal detector is configured to detect an analog signal obtained by subtracting a component of the resonant frequency from the MR signals amplified by the pre-amplifier. The A/D converter is configured to generate the MR signal data by converting the analog signal detected by the signal detector into a digital signal and to output the generated MR signal data to the processing circuitry 14.

The gantry 9 has a bore 9a that is hollow and is formed to have a substantially circular cylindrical shape (which may have an oval cross-section orthogonal to the central axis thereof). The gantry 9 is configured to support the static magnetic field magnet 1, the gradient coil 2, and the whole body coil 4. More specifically, the gantry 9 is supporting the static magnetic field magnet 1, the gradient coil 2, and the whole body coil 4, while the gradient coil 2 is arranged on the inner circumferential side of the static magnetic field magnet 1, the whole body coil 4 is arranged on the inner circumferential side of the gradient coil 2, and the bore 9a is arranged on the inner circumferential side of the whole body coil 4. In this situation, the space formed on the inside of the bore 9a of the gantry 9 serves as the imaging space in which the subject S is placed when an imaging process is to be performed on the subject S.

In the present example, the configuration is explained in which the MRI apparatus 100 has a so-called tunnel-like structure where the static magnetic field magnet 1, the gradient coil 2, and the whole body coil 4 are each formed to have a substantially circular cylindrical shape; however, possible embodiments are not limited to this example. For instance, the MRI apparatus 100 may have a so-called open structure where a pair of static magnetic field magnets, a pair of gradient coils, and a pair of RF coils are each arranged so as to face each other while the imaging space in which the subject S is placed is interposed therebetween. In that situation, the space interposed between the pair of static magnetic field magnets, the pair of gradient coils, and the pair of RF coils corresponds to the bore in the tunnel-like structure.

The interface 10 is configured to receive operations to input various types of instructions and various types of information from the operator. More specifically, the interface 10 is connected to the processing circuitry 16 and is configured to convert the input operations received from the operator into electrical signals and to output the electrical signals to the processing circuitry 16. For example, the interface 10 may be realized by using a trackball, a switch button, a mouse, a keyboard, a touch-pad on which an input operation can be performed by touching the operation surface thereof, a touch-screen in which a display screen and a touch-pad are integrally formed, a contactless input circuit using an optical sensor, an audio input circuit, and/or the like that are used for setting an imaging condition, a Region of Interest (ROI), and the like. In the present disclosure, the interface 10 does not necessarily have to include one or more physical operational component parts such as a mouse, a keyboard, and/or the like. Examples of the interface 10 include, for instance, electrical signal processing circuitry configured to receive an electrical signal corresponding to an input operation from an external input device provided separately from the apparatus and to output the electrical signal to a controlling circuit.

The display 11 is configured to display various types of information and various types of images. More specifically, the display 11 is connected to the processing circuitry 16 and is configured to convert data of the various types of information and the various types of images sent thereto from the processing circuitry 16 into display-purpose electrical signals and to output the electrical signals. For example, the display 11 may be realized by using a liquid crystal monitor, a Cathode Ray Tube (CRT) monitor, a touch-panel, or the like.

The storage 12 is configured to store various types of data therein. More specifically, the storage 12 is configured to store the MR signal data and image data therein. For example, the storage 12 may be realized by using a semiconductor memory element such as a Random Access Memory (RAM), a flash memory, or the like, a hard disk, an optical disk, or the like.

The processing circuitry 13 includes a couch controlling function 13a. The couch controlling function 13a is configured to control operations of the couch 6 by outputting a control-purpose electrical signal to the couch 6. For example, via the interface 10, the couch controlling function 13a is configured to receive an instruction to move the couchtop 6a in a longitudinal direction, an up-and-down direction, or a left-and-right direction from the operator and to operate a moving mechanism for the couchtop 6a included in the couch 6 so as to move the couchtop 6a according to the received instruction.

The processing circuitry 14 includes a data acquiring function 14a. The data acquiring function 14a is configured to acquire the MR signal data of the subject S by executing various types of pulse sequences. More specifically, the data acquiring function 14a executes a pulse sequence by driving the gradient power source 3, the transmitter circuitry 7, and the receiver circuitry 8 according to sequence execution data output from the processing circuitry 16. In this situation, the sequence execution data is data representing the pulse sequence and is information that defines: the timing with which the electric current is to be supplied from the gradient power source 3 to the gradient coil 2 and the intensity of the electric current to be supplied; the intensity of the RF pulse signal to be supplied from the transmitter circuitry 7 to the whole body coil 4 and the timing with which the RF pulse signal is to be supplied; the detection timing with which the MR signals are to be detected by the receiver circuitry 8, and the like. Further, as a result of executing the pulse sequence, the data acquiring function 14a receives the MR signal data from the receiver circuitry 8 and stores the received MR signal data into the storage 12. In this situation, a set made up of pieces of MR signal data received by the data acquiring function 14a is stored in the storage 12 as data structuring a k-space as a result of being arranged two-dimensionally or three-dimensionally according to the position information appended thereto by the readout gradient magnetic field, the phase encoding gradient magnetic field, and the slice gradient magnetic field explained above.

The processing circuitry 15 includes an image generating function 15a. The image generating function 15a is configured to generate an image on the basis of the MR signal data stored in the storage 12. More specifically, the image generating function 15a generates the image by reading the MR signal data stored in the storage 12 by the data acquiring function 14a and further performing a post-processing process, i.e., a reconstructing process (such as a Fourier transform or the like) on the read MR signal data. Further, the image generating function 15a stores image data of the generated image into the storage 12.

The processing circuitry 16 includes a main controlling function 16a. By controlling constituent elements of the MRI apparatus 100, the main controlling function 16a is configured to exercise overall control of the MRI apparatus 100. More specifically, the main controlling function 16a causes the display 11 to display a Graphical User Interface (GUI) used for receiving the operations to input the various types of instructions and the various types of information from the operator. Further, in response to the input operations received via the interface 10, the main controlling function 16a controls the constituent elements of the MRI apparatus 100. For example, the main controlling function 16a receives an input of an imaging condition from the operator via the interface 10. Further, the main controlling function 16a executes various types of pulse sequences by generating sequence execution data on the basis of the received imaging condition and transmitting the generated sequence execution data to the processing circuitry 14. Further, for example, in response to a request from the operator, the main controlling function 16a reads image data from the storage 12 and outputs the read image data to the display 11.

An overall configuration of the MRI apparatus 100 according to the present embodiment has thus been explained. The MRI apparatus 100 according to the present embodiment structured as explained above is capable of imaging various regions of the subject S by using various types of scans while setting appropriate imaging conditions. Further, the MRI apparatus 100 according to the present embodiment is configured to be able to perform a differential diagnosis process on various types of disease patterns, by using the various types of images acquired from the imaging processes.

In this regard, generally speaking, in differential diagnosis processes performed at hospitals and the like, location in the subject's body that is suspicious or related to a diagnosis is determined through an interview with a medical doctor or the like, and subsequently, an imaging process performed on the determined location. Further, after an analysis is performed on the basis of one or more images acquired from the imaging process, a diagnosis is made. Further, when it is not possible to make a diagnosis from the imaged location alone, another imaging method such as imaging another location is considered, and an imaging process is performed again.

Usually, however, there are only a limited number of MRI apparatuses installed in a hospital or the like, and the subject may need to wait for an appointment for the next medical examination, in some situations. In those situations, because it is not possible to promptly perform the imaging process for the second time, it may be difficult in some situations to efficiently proceed with the differential diagnosis process.

To cope with this situation, the MRI apparatus 100 according to the present embodiment is configured to be able to efficiently perform imaging processes required by the differential diagnosis process.

More specifically, the MRI apparatus 100 according to the present embodiment includes an imager, a storage, an obtaining unit, and an output controlling unit.

In the present embodiment, the imager is realized with the static magnetic field magnet 1, the gradient coil 2, the gradient power source 3, the whole body coil 4, the local coil 5, the couch 6, the transmitter circuitry 7, the receiver circuitry 8, and the gantry 9. In the following sections, the static magnetic field magnet 1, the gradient coil 2, the gradient power source 3, the whole body coil 9, the local coil 5, the couch 6, the transmitter circuitry 7, the receiver circuitry 8, and the gantry 9 will collectively be called the imager. Further, in the present embodiment, the obtaining unit is realized with an obtaining function 16b included in the processing circuitry 16. Also, in the present embodiment, the output controlling unit is realized with an output controlling function 16c included in the processing circuitry 16.

The imager is configured to image the subject by performing a first scan. In the present embodiment, the imager images the subject by implementing magnetic resonance imaging.

The storage 12 stores therein a correspondence relationship among each of a plurality of disease patterns, a plurality of scans used for performing a differential diagnosis process on the disease pattern, and a plurality of regions used for performing the differential diagnosis process on the disease pattern. In this situation, the correspondence relationship stored in the storage 12 is set on the basis of, for example, sets each made up of scans and regions that were used for performing differential diagnosis processes on disease patterns during diagnoses, studies, and the like in the past.

On the basis of first image data acquired from the first scan, the obtaining function 16b is configured to obtain a disease pattern having a possibility of being applicable to the subject and a first index value indicating a degree of applicability of the disease pattern. In this situation, the obtaining function 16b obtains the disease pattern having the possibility of being applicable to the subject and the first index value indicating the degree of applicability of the disease pattern, on the basis of a first region included in the first image data acquired from the first scan. For example, the obtaining function 16b performs a process of dividing a brain region included in the first image data into a plurality of regions and obtains the first index value in accordance with a result of the dividing process.

Further, on the basis of second image data acquired from a second scan, the obtaining function 16b, again, obtains a disease pattern having a possibility of being applicable to the subject and a second index value indicating a degree of applicability of the disease pattern. In this situation, the second scan is for acquiring image data that enables an analysis capable of improving the level of precision of the diagnosis in the differential diagnosis process, in comparison to the situation where only an analysis using the image data acquired from the first scan is performed. For example, the level of precision of the diagnosis is expressed by sensitivity (the ratio of people being positive among people with the disease), specificity (the ratio of people being negative among people with the disease), or the like.

When it is possible to perform the differential diagnosis process on the disease pattern on the basis of the first index value obtained by the obtaining function 16b, the output controlling function 16c is configured to output information indicating the disease pattern to the display 11.

On the contrary, when it is not possible to perform the differential diagnosis process the disease pattern, on the basis of the first index value obtained by the obtaining function 16b, the output controlling function 16c is configured to output an imaging condition used for causing the imager to image the subject by performing the second scan different from the first scan, on the basis of the correspondence relationship stored in the storage 12 and the disease pattern having the possibility of being applicable to the subject and having been obtained by the obtaining function 16b. In this situation, the output controlling function 16c identifies a second region different from the first region on the basis of the correspondence relationship stored in the storage 12 and the disease pattern having the possibility of being applicable to the subject and having been obtained by the obtaining function 16b and further outputs the imaging condition used for causing the imager to image the second region of the subject by performing the second scan. In this situation, the second region is a region that enables an analysis capable of improving the level of precision of the diagnosis in the differential diagnosis process, in comparison to the situation where only an analysis related to the first region is performed. Further, the output controlling function 16c is configured to output the first image data, the second image data, and information indicating the disease pattern having the possibility of being applicable to the subject, to the display 11. Further, the output controlling function 16c is configured to store the first image data and the second image data into the storage 12, as pieces of image data acquired from mutually the same medical examination.

In this situation, the output controlling function 16c causes the imager to perform the first scan and the second scan while the subject is kept on the couch 6.

In the following sections, as an example of the differential diagnosis process using the MRI apparatus 100 according to the present embodiment, an example will be explained in which a differential diagnosis process is performed for Alzheimer's disease.

Differential diagnosis processes for Alzheimer's disease are performed, for example, by measuring the volume of the hippocampus while using a Magnetization Prepared Rapid Gradient Echo (MPRAGE) image. Together therewith, it is known that sensitivity and specificity can be improved by additionally performing an analysis that uses a Magnetic Resonance Spectroscopy (MRS) image of the posterior cingulum.

Accordingly, for example, as the correspondence relationship among each of the disease patterns, the plurality of scans, and the plurality of regions described above, the storage 12 stores therein a correspondence relationship among Alzheimer's disease, MPRAGE and MRS scans, and the hippocampus and the posterior cingulum. In this situation, the MPRAGE scan is an example of the first scan mentioned above; the MRS scan is an example of the second scan mentioned above; the hippocampus is an example of the first region mentioned above; and the posterior cingulum is an example of the second region mentioned above.

Figure 2:
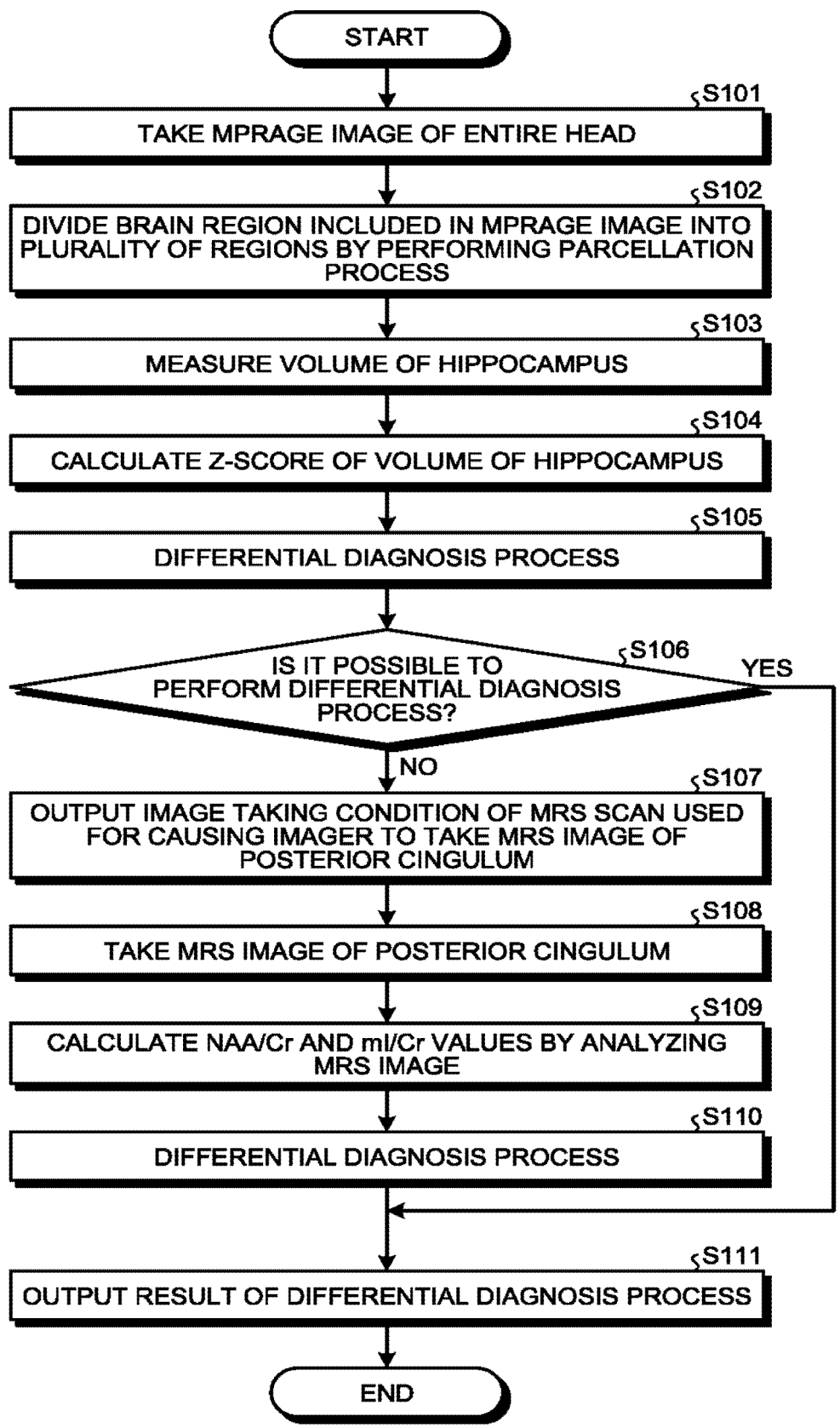
FIG. 2 is a flowchart illustrating a flow in a process performed by the MRI apparatus according to the first embodiment.

FIG. 2 is a flowchart illustrating a flow in a process performed by the MRI apparatus 100 according to the first embodiment.

For example, as illustrated in FIG. 2, to perform a differential diagnosis process for Alzheimer's disease, the imager at first takes an MPRAGE image of the entire head of the subject, by performing a Magnetization Prepared Rapid Gradient Echo (MPRAGE) scan (step S101).

Subsequently, the obtaining function 16b divides the brain region included in the MPRAGE image taken by the imager into a plurality of regions by performing a parcellation process (step 2102).

Figure 3:
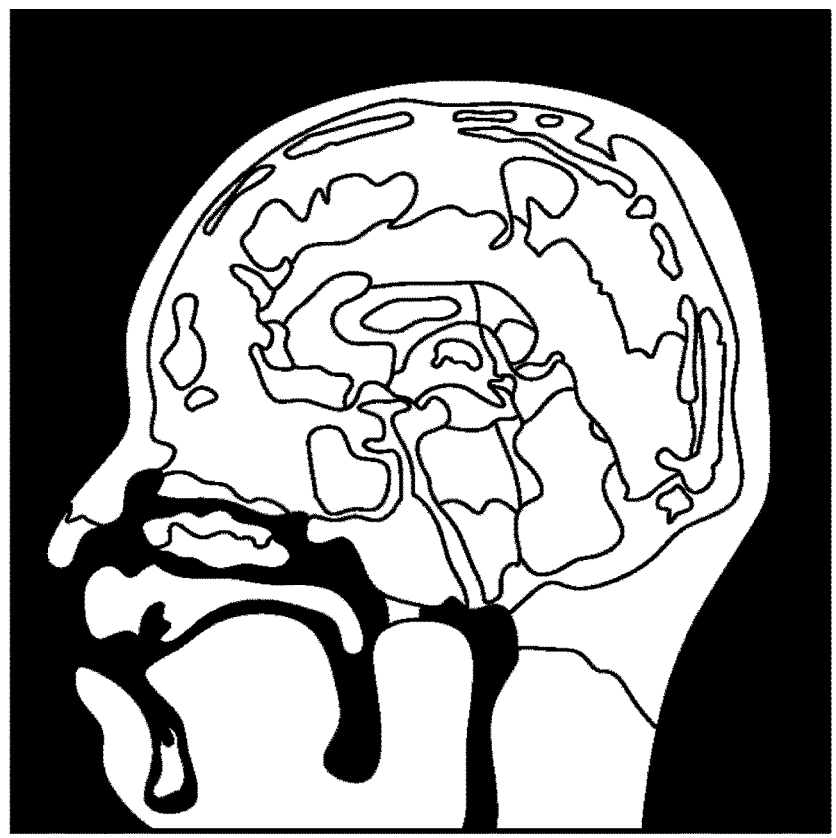
FIG. 3 is a drawing illustrating an example of a brain region dividing process performed by an obtaining function according to the first embodiment.

FIG. 3 is a drawing illustrating an example of the brain region dividing process performed by the obtaining function 16b according to the first embodiment.

For example, as illustrated in FIG. 3, the obtaining function 16b divides the brain region included in the MPRAGE image into the plurality of regions sectioned on the basis of anatomical structures, functions, and the like, by performing the parcellation process while using the MPRAGE image of the entire head. For example, the obtaining function 16b divides the brain region into regions corresponding to the hippocampus, the amygdala, the posterior cingulum, the parahippocampal gyrus, the entorhinal area, and the like.

Returning to the description of FIG. 2, the obtaining function 16b subsequently measures the volume of the hippocampus on the basis of the MPRAGE image (step 3103). Further, the obtaining function 16b calculates a Z-score of the volume of the hippocampus measured from the MPRAGE image, on the basis of a hippocampus normal curve expressing a relationship between volumes of the hippocampus in normal brains and ages of people, as well as the age of the subject (step 104). In that situation, the volume of the hippocampus and the Z-score serve as an example of the first index value mentioned above.

After that, on the basis of the calculated Z-score of the volume of the hippocampus, the obtaining function 16b performs a differential diagnosis process for Alzheimer's disease (step S105).

Figure 4:
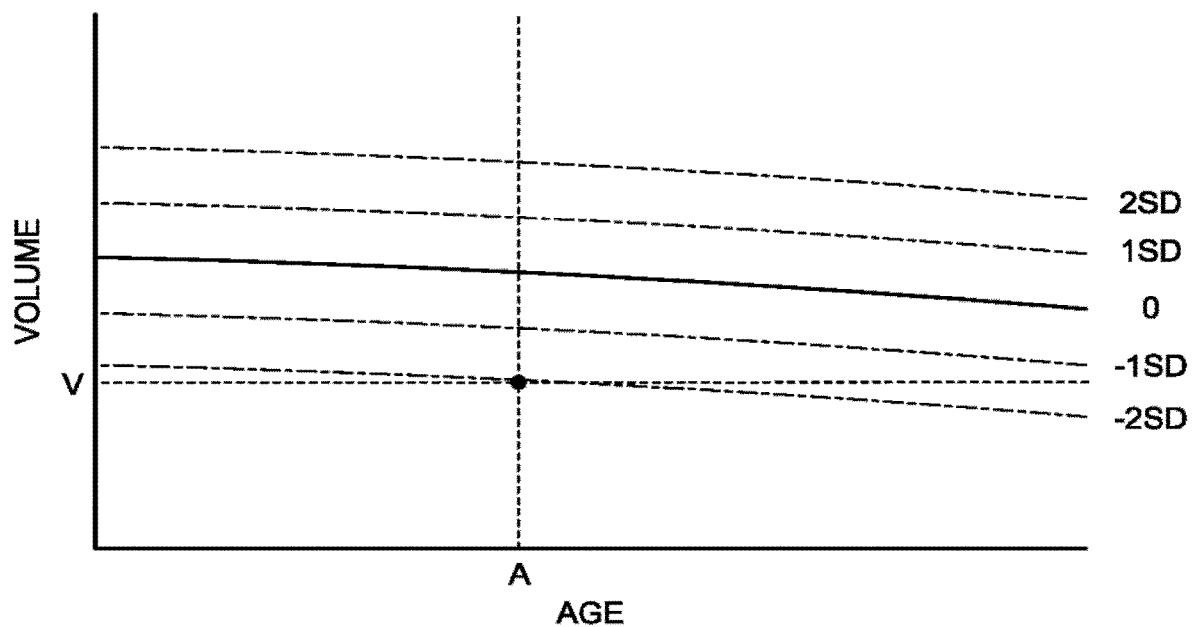
FIG. 4 is a drawing illustrating an example of a differential diagnosis process performed by the obtaining function according to the first embodiment.

FIG. 4 is a drawing illustrating an example of the differential diagnosis process performed by the obtaining function 16b according to the first embodiment.

In the present example, FIG. 4 illustrates a distribution of Z-scores calculated on the basis of the hippocampus normal curve. More specifically, the curve in a solid line in FIG. 4 is a normal curve of the hippocampi (where the Z-score is 0). The plurality of curves each indicated with a dashed line above and below the normal curve express volumes and ages with which the Z-score is equal to Standard Deviation (SD), 1SD, −1SD, and −2SD, in the stated order starting from the top.

For example, the obtaining function 16b sets a range which has a predetermined size and in which Z-scores are close to −2SD, as a reference range. Further, when the Z-score calculated on the basis of the MPRAGE image is smaller than the lower limit value of the reference range, the obtaining function 16b considers that the hippocampus is statistically more atrophied than a normal brain and determines that the subject has Alzheimer's disease. In that situation, the obtaining function 16b obtains occurrence of Alzheimer's disease, as a disease pattern having a possibility of being applicable to the subject. On the contrary, when the score calculated on the basis of the MPRAGE image is larger than the upper limit value of the reference range, the obtaining function 16b determines that the subject does not have Alzheimer's disease. Further, when the Z-score calculated on the basis of the MPRAGE image falls within the reference range, the obtaining function 16b does not perform the process of judging whether or not the subject has Alzheimer's disease.

In other words, the obtaining function 16b determines that it is possible to perform the differential diagnosis process for Alzheimer's disease (to judge whether or not the subject has Alzheimer's disease), when the Z-score calculated on the basis of the MPRAGE image is outside the reference range. On the contrary, the obtaining function 16b determines that it is not possible to perform the differential diagnosis process for Alzheimer's disease, when the score calculated on the basis of the MIRAGE image is within the reference range. For example, in the example in FIG. 4, when the volume is equal to V and the age is equal to A, because the score is equal to −2 SD, it is determined that it is not possible to perform the differential diagnosis process for Alzheimer's disease.

In the present example, the situation in which "it is possible to perform a differential diagnosis process" does not necessarily have to be a situation in which it is possible to perform a differential diagnosis process in a strict sense, hut may be a situation in which the circumstance is sufficient for performing the differential diagnosis process. Similarly, the situation in which "it is not possible to perform a differential diagnosis process" does not necessarily have to be a situation in which it is impossible to perform a differential diagnosis process in a strict sense, but may be a situation in which the circumstance is not sufficient for performing the differential diagnosis process.

Further, the method for judging whether or not it is possible to perform the differential diagnosis process for Alzheimer's disease is not limited to the example described above. For instance, it is also acceptable to judge whether or not it is possible to perform the differential diagnosis process by using either a past image or past measured result of the same subject. In that situation, for example, the obtaining function 16b reads the past image or the past measured result of the same subject from the storage 12 and obtains the volume of the hippocampus from the past with respect to the same subject. Further, the obtaining function 16b compares the volume of the hippocampus the past with the volume of the hippocampus at present. The obtaining function 16b determines that the subject does not have Alzheimer's disease when the volume has not changed and determines that the subject has Alzheimer's disease when the change amount in the volume is equal to or larger than a predetermined value. Further, when the change in the volume is smaller than the predetermined value, the obtaining function 16b determines that it is not possible to perform the differential diagnosis process for Alzheimer's disease.

Further, for example, another arrangement is also acceptable in which the operator (e.g., a medical doctor) judges whether or not it is possible to perform a differential diagnosis process for Alzheimer's disease. In that situation, for example, the obtaining function 16b causes the display 11 to display information necessary for performing the differential diagnosis process such as the MPRAGE image, the measured volume of the hippocampus, the calculated score of the volume of the hippocampus, and the like. After that, the obtaining function 16b receives, from the operator, an input of a judgment result indicating whether or not it is possible to perform the differential diagnosis process, via the interface 10.

Returning to the description of FIG. 2, when it is determined that it is possible to perform the differential diagnosis process for Alzheimer's disease (step S106: Yes), the output controlling function 16c subsequently outputs result of the differential diagnosis process performed by the obtaining function 16b to the display 11 (step S111). For example, as the result of the differential diagnosis process, the output controlling function 16c outputs the MIRAGE image and information indicating that the subject has Alzheimer's disease (or does not have Alzheimer's disease) to the display 11.

On the contrary, when it is determined that it is not possible to perform the differential diagnosis process for Alzheimer's disease (step S106: No), the output controlling function 16c outputs, to he main controlling function 16a, an imaging condition of an MRS scan used for causing the imager to take an MRS image of the posterior cingulum, on the basis of the correspondence relationship stored in the storage 12 (step S107). In this situation, the imaging condition output to the main controlling function 16a includes position information of the posterior cingulum obtained by performing the parcellation process explained above.

Subsequently, under control of the main controlling function 16a, the imager takes the MRS image of the posterior cingulum, on the basis of the imaging condition of the MRS scan that was output from the output controlling function 16c (step 108).

After that, the obtaining function 16b analyzes the MRS image taken by the imager and calculates a N-acetylaspartate/Creatine (NAA/Cr) value and a myo-inositol/Creatine (mI/Cr) value of the posterior cingulum (step S109). In this situation, the NAA/Cr value and the mI/Cr value serve as an example of the second index value mentioned above.

Further, on the basis of the NAA/Cr value and the mI/Cr value of the posterior cingulum that were calculated, the obtaining function 16b performs a differential diagnosis process for Alzheimer's disease (step S110). For example, the obtaining function 16b performs the differential diagnosis process for Alzheimer's disease, on the basis of changes in the NAA/Cr and m values, as compared to NAA/Cr and mI/Cr values of the posterior cingulum of the same subject calculated in the past.

After that, the output controlling function 16c output a result of the differential diagnosis process performed by the obtaining function 16b, to the display 11 (step S111). For example, as the result of the differential diagnosis process, the output controlling function 16c outputs the MPRAGE image, the MRS image, and information indicating that the subject has Alzheimer's disease (or does not have Alzheimer's disease), to the display 11. Further, the output controlling function 16c stores the MPRAGE image and the MRS image into the storage 12, as images acquired from mutually the same medical examination.

In the series of processes described above, the output controlling function 16c causes the imager to perform the MPRAGE scan and the MRS scan while the subject is kept on the couch 6. As a result, with the single session of medical examination (exam), it is possible to perform the differential diagnosis process that was unable to reach a diagnosis by measuring the volume of the hippocampus alone.

In the example described above, as for the differential diagnosis process based on the NAA/Cr and mI/Cr values of the posterior cingulum, it is not judged whether or not it is possible to perform the differential diagnosis process; however, possible embodiments are not limited to this example. For instance, similarly to the differential diagnosis process based on the score of the volume of the hippocampus, it is also acceptable to judge whether or not it is possible to perform the differential diagnosis process, also for the differential diagnosis process based on the NAA/Cr and mI/Cr values of the posterior cingulum. In that situation, for example, the storage 12 stores therein, as the scans and the regions kept in correspondence with Alzheimer's disease, one or more scans and regions that enable an analysis capable of further improving the level of precision of the diagnosis in the differential diagnosis process, in addition to the MPRAGE scan, the MRS scan, the hippocampus, and the posterior cingulum. Further, when it is determined to be impossible to perform the differential diagnosis process based on the NAA/Cr and mI/Cr values of the posterior cingulum, the output controlling function 16c causes the imager to perform an additional imaging process on the basis of the correspondence relationship stored in the storage 12, so that the obtaining function 16b performs a differential diagnosis process by analyzing the image acquired from the imaging process. In this manner, the obtaining function 16b and the output controlling function 16c cause the imager to perform imaging processes by using the plurality of scans and the plurality of regions kept in correspondence with Alzheimer's disease, until it becomes possible to perform a differential diagnosis process. Further, when it becomes possible to perform a differential diagnosis process, the obtaining function 16b outputs a result of the differential diagnosis process to the display 11. On the contrary, when it is still impossible to perform a differential diagnosis process after performing the imaging processes using all the scans and the regions, the obtaining function 16b outputs information indicating that it is impossible to perform the differential diagnosis process to the display 11, and the process is thus ended.

Further, in the description above, the example is explained in which the first scan is the MPRAGE scan, whereas the second scan is the MRS scan, while the first region is the hippocampus, whereas the second region is the posterior cingulum; however, possible embodiments are not limited to this example. For instance, as long as the second scan is able to improve the level of precision of the diagnosis in the differential diagnosis process in comparison to that of an analysis performed by using the image data acquired from the first scan, the second scan may be a scan to acquire T2-weighted image or a scan to acquire a FLuid-Attenuated Inversion Recovery (FLAIR) image. Further, the second region does not necessarily have to the posterior cingulum and may be another region. Furthermore, the first scan does not necessarily have to be different from the second scan. The first region does not necessarily have to be different from the second region. For example, it is acceptable to arrange the first scan and the second scan to be mutually the same type of scan, while arranging the first region to be different from the second region. Alternatively, it is acceptable to arrange the first scan and the second scar to be mutually-different types of scans, while arranging the first region to be the same as the second region.

Further, in the description above, the example is explained in which the differential diagnosis process is performed for Alzheimer's disease; however, possible embodiments are not limited to this example. In other words, disease patterns for which the MRI apparatus 100 is capable of performing differential diagnosis processes are not limited to Alzheimer's disease. It is possible to perform differential diagnosis processes on various types of disease patterns by using the same processes as described above.

In the configuration illustrated in FIG. 1, it is possible to realize the processing circuitries 13 to 16 by using one or more processors, for example. In that situation, the processing functions of the processing circuitries are stored in the storage 12 in the form of computer-executable programs, for example. Further, the processing circuitries realize the functions corresponding to the programs by reading and executing the programs from the storage 12. In other words, the processing circuitries that have read the programs have the processing functions illustrated in FIG. 1. In this situation, the processing circuitries may be structured by using a plurality of processors, so that the processing functions thereof are realized as a result of the processors executing the programs. Further, the processing functions of the processing circuitries may be realized as being distributed to a plurality of processing circuitries or as being integrated together into a single piece of processing circuitry, as appropriate. Further, in the above description, the example is explained in which the single storage (i.e., the storage 12) is configured to store therein the programs corresponding to the processing functions; however, another arrangement is also acceptable in which a plurality of storages are provided in a distributed manner, so that the processing circuitries read a corresponding one of the programs from a corresponding one of the individual storages.

For example, among the process illustrated in FIG. 2, the processes at steps S102 through S105, S109, and S110 are realized as a result of, for example, the processing circuitry 16 reading and executing a predetermined program corresponding to the obtaining function 16*b* from the storage 12. Further, the processes at steps S106, S107, and S111 are realized as a result of, for example, the processing circuitry 16 reading and executing a predetermined program corresponding to the output controlling function 16*c* from the storage 12.

As explained above, in the first embodiment, while the subject is kept on the couch 6, the differential diagnosis process is performed on the disease pattern, on the basis of the first image data acquired from the first scan. When it is not possible to perform the differential diagnosis process, the second scan is further performed to take the second image data capable of improving the level of precision of the diagnosis in the differential diagnosis process. With these arrangements, the single session of medical examination is able to acquire all the pieces of image data required by the differential diagnosis process. Further, it is possible to automatically execute the imaging process performed for the second time required by the differential diagnosis process. Consequently, according to the first embodiment, it is possible to efficiently perform the imaging processes required by the differential diagnosis process.

A Modification Example of First Embodiment

The first embodiment described above may be carried out by changing a part of the configuration or the processes of the MRI apparatus 100. Thus, a modification example of the first embodiment will be explained below, while a focus is placed on differences from the first embodiment.

For example, in the first embodiment above, the example is explained in which the correspondence relationship stored in the storage 12 is set on the basis of the sets each made up of scans and regions that were used for performing differential diagnosis processes on disease patterns during diagnoses, studies, and the like in the past; however, possible embodiments are not limited to this example. For instance, the correspondence relationship stored in the storage 12 may be set on the basis of text data saved in a Vencor Neutral Archive (VNA) or information about additional diagnosis processes recorded in Electronic Medical Records (EMRs).

Figure 5:
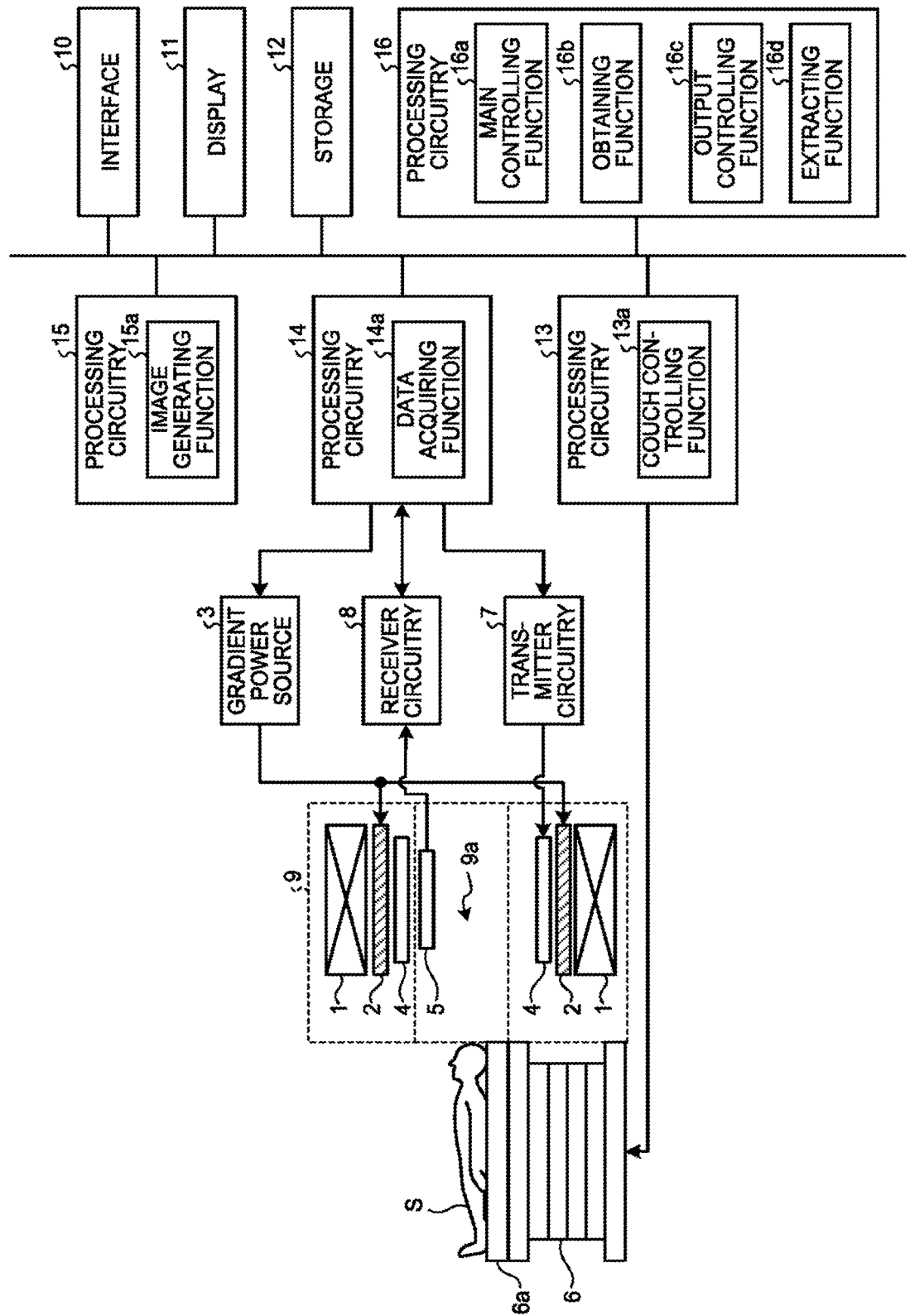
FIG. 5 is a diagram illustrating a configuration f an MRI apparatus according to a modification example of the first embodiment.

FIG. 5 is a drawing illustrating a configuration of an MRI apparatus according to a modification example of the first embodiment.

In this situation, for example, the processing circuitry 16 of the MRI apparatus 100 further includes an extracting function 16*d*, as illustrated in FIG. 5.

The extracting function 16*d* is configured to obtain one or more documents describing relevance between disease patterns and either a plurality of scans or a plurality of regions used for performing a differential diagnosis process on each of the disease patterns, to extract a correspondence relationship between each of the disease patterns, the plurality of scans, and the plurality of regions, by performing a text analysis on the documents, and to store the extracted correspondence relationship into the storage 12.

For example, the extracting function 16*d* obtains either text data or electronic medical record data from either a VNA system or an electronic medical record system that is connected to the MRI apparatus 100 via a network. Further, the extracting function 16*d* extracts the information about the additional diagnosis process by performing a text analysis using natural language processing on the obtained text data or electronic medical record data. In this situation, the text data represents one or more academic papers or the like, for example, from which the extracting function 16*d* extracts the information about the additional diagnosis process having a correlation with the generally-known fact about the relationship between a decrease in the volume of the hippocampus and Alzheimer's disease. Further, on the basis of the extracted information about the additional diagnosis process, the extracting function 6*d* sets the correspondence relationship to be stored into the storage 12.

Further, in the first embodiment above, the example is explained in which the plurality of scans kept in correspondence with the disease pattern are sequentially executed until it becomes possible to perform a differential diagnosis process; however, possible embodiments are not limited to this example. For instance, another arrangement is also acceptable in which levels of priority are set with the scans kept in correspondence with the disease pattern so that, when it is not possible to perform a differential diagnosis process on the basis of the image data acquired from the first scan, a second scan to be performed next is selected from among the other plurality of scans on the basis of the levels of priority.

In that situation, together with the correspondence relationship among the disease pattern, the plurality of scans, and the plurality of regions, the storage 12 further stores therein the levels of priority of the scans. In this situation, the priority level of each of the scans is set so as to indicate, for example, a degree of effectiveness in consideration of the time it takes to perform the scan and an analysis, as well as an increasing ratio for the level of precision of the diagnosis.

Further, on the basis of the levels of priority stored in the storage 12, the output controlling function 16c selects the second scan. For example, the output controlling function 16c causes the display 11 to display information indicating the plurality of scans serving as candidates for the second scan, in descending order of the levels of priority of the scans. After that, via the interface 10, the output controlling function 16c receives, from the operator, an operation to select a scan to be executed as the second scan from among the plurality of scans being displayed.

In the first embodiment above, the example is explained in which the configuration of the medical image diagnosis apparatus of the present disclosure applied to the MRI apparatus; however, possible embodiments are no limited to this example. For instance, the configuration of the medical image diagnosis apparatus of the present disclosure may be applied to an X-ray Computed Tomography (CT) apparatus, a Positron Emission Tomography (PET) apparatus, an X-ray diagnosis apparatus, or the like. In that situation, processing circuitry of a console device or the like included in the X-ray CT apparatus, the PET apparatus, the X-ray diagnosis apparatus, or the like is configured so as to include the obtaining function 16b, the output controlling function 16c, and the extracting function 16d described above.

Further, in the MRI apparatus 100 according to the first embodiment above, the example is explained in which, when it is not possible to perform the differential diagnosis process on the disease pattern on the basis of the first index value, the output controlling function 16c causes the imager to perform the second scan by directly outputting the imaging condition of the second scan to the main controlling function 16a; however, possible embodiments are not limited to this example. For instance, another arrangement is also acceptable in which, when imaging processes performed by medical image diagnosis apparatuses are managed by a medical examination appointment system at a hospital or the like, an additional order (an order for an additional medical examination) including the imaging condition of the second scan is registered into a queue of the medical examination system. For example, the medical examination appointment system in this situation may be a Radiology Information System (RIS) or the like.

In that situation, when it is not possible to perform the differential diagnosis process on the disease pattern on the basis of the first index value, the output controlling function 16c registers the additional order including the imaging condition used for imaging the subject by performing the second scan, into the medical examination appointment system. After that, when the operator (a medical doctor, a medical technologist, or the like) of the medical examination appointment system agrees to the additional order, the output controlling function 16c causes the imager to image the subject by performing the second scan.

In this situation, for example, another arrangement is also acceptable in which the output controlling function 16c obtains costs (the imaging taking time period, the fee for the imaging process, whether a contrast agent and X-ray exposure are involved or not, etc.) of the imaging process in the second scan and, when the obtained costs satisfy a predetermined condition, the output controlling function 16c registers the additional order for the second scan into the medical examination appointment system.

Further, in the first embodiment above, the example is explained in which the MRI apparatus 100 performs the first scan and the second scan. However, possible embodiments are not limited to this example. For instance, it is acceptable to cause another medical image diagnosis apparatus to perform the second scan. In this situation, the other medical image diagnosis apparatus may be, for example, an X-ray Computed Tomography (CT) apparatus, a Positron Emission Tomography (PET) apparatus, an X-ray diagnosis apparatus, or the like.

In that situation, when it is not possible to perform the differential diagnosis process on the disease pattern on the basis of the first index value obtained by the obtaining function 16b, the output controlling function 16c transmits, to the other medical image diagnosis apparatus, an imaging condition used for imaging the subject by performing the second scan different from the first scan, on the basis of the correspondence relationship stored in the storage 12 and the disease pattern having a possibility of being applicable to the subject and having been obtained by the obtaining function 16b.

In this situation, the output controlling function 16c may directly transmit the imaging condition to the other medical image diagnosis apparatus. Alternatively, when imaging processes performed by medical image diagnosis apparatuses are managed by a medical examination appointment system at a hospital or the like, the output controlling function 16c may indirectly transmit the imaging condition to the other medical image diagnosis apparatus by registering an additional order including the imaging condition into a queue of the medical examination appointment system.

Further, in that situation, the obtaining function 16b obtains image data taken by the other medical image diagnosis apparatus, so as to perform a differential diagnosis process on the basis of the obtained image data.

Second Embodiment

Next, as a second embodiment, an example of a medical image diagnosis system of the present disclosure will be explained. In the present embodiment, an example in which the medical image diagnosis apparatus is an MRI apparatus will be explained.

Figure 6:
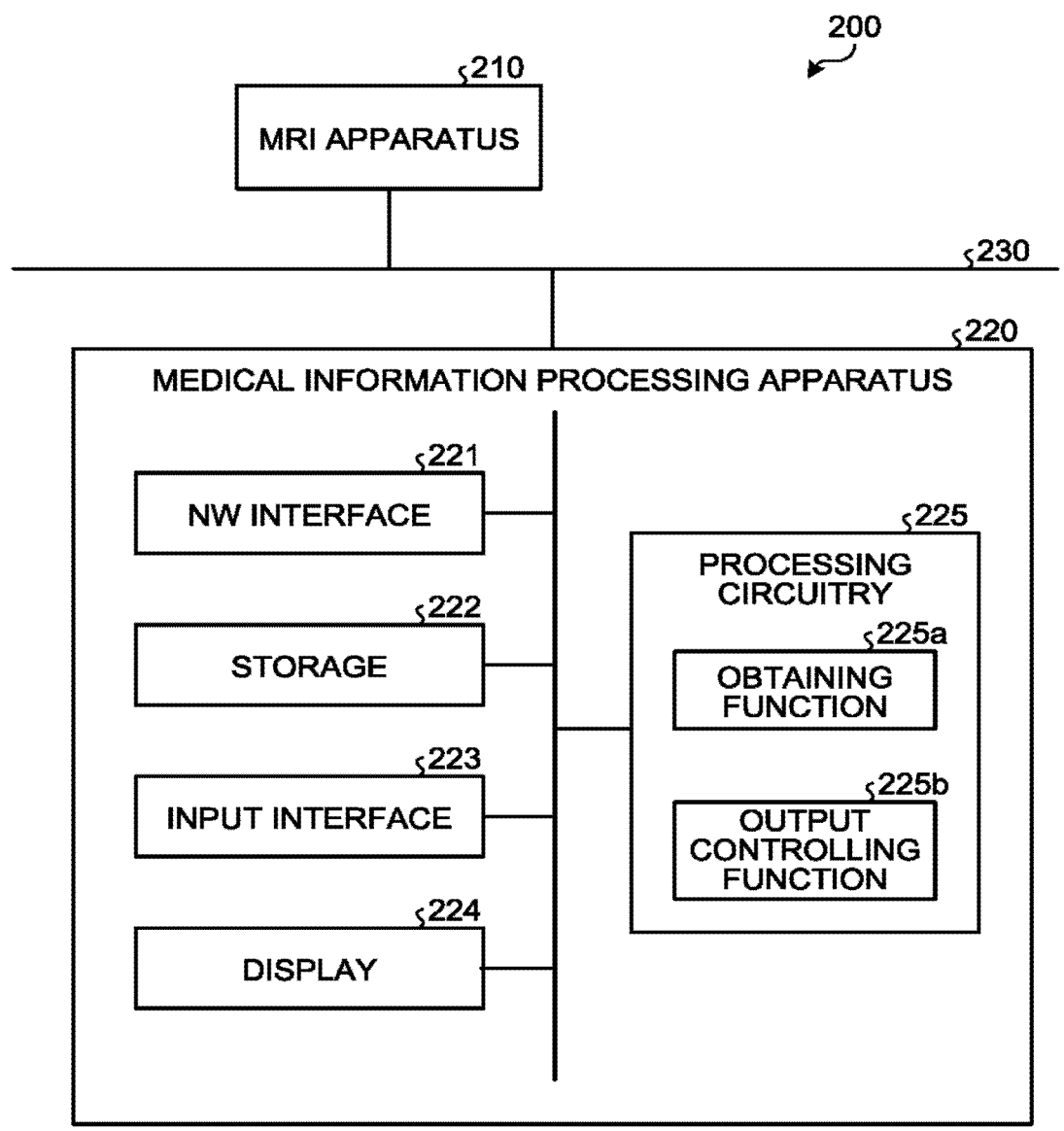
FIG. 6 is a diagram illustrating a configuration of medical image diagnosis system according to a second embodiment.

FIG. 6 is a diagram illustrating a configuration of medical image diagnosis system according to the second embodiment.

For example, as illustrated in FIG. 6, a medical image diagnosis system 200 according to the present embodiment includes an MRI apparatus 210 and a medical information processing apparatus 220. For example, the medical image diagnosis system 200 according to the present embodiment is installed in a medical institution such as a hospital or a clinic. In the medical image diagnosis system 200, the MRI apparatus 210 and the medical information processing apparatus 220 are connected together so as to be able to communicate with each other, via a network 230 such as an intra-hospital Local Area Network (LAN).

The MRI apparatus 210 is configured to acquire image data of a subject by using a magnetic resonance phenomenon. More specifically, the MRI apparatus 210 has almost the same configuration as that of the MRI apparatus 100 explained in the first embodiment, except for the obtaining function 16b, the output controlling function 16c, and the extracting function 16d.

The medical information processing apparatus 220 10 configured to obtain various types of information from the MRI apparatus 210 via the network 230 and to perform various types of information processing processes by using the obtained information. For example, the medical information processing apparatus 220 may be realized by using a computer device such as a server, a workstation, a personal computer, a tablet terminal, or the like.

More specifically, the medical information processing apparatus 220 includes a network (NW) interface 221, a storage 222, an input interface 223, a display 224, and processing circuitry 225.

The NW interface 221 is connected to the processing circuitry 225 and is configured to control communication performed between the medical information processing apparatus 220 and the MRI apparatus 210. More specifically, the NW interface 221 receives image data from the MRI apparatus 210 and outputs the received information to the processing circuitry 225. For example, the NW interface 221 may be realized by using a network card, a network adaptor, a Network Interface Controller (NIC), or the like.

The storage 222 is connected to the processing circuitry 225 and is configured to store therein various types of data. For example, the storage 222 may be realized by using a semiconductor memory element such as a Random Access Memory (RAM), a flash memory, or the like, a hard disk, an optical disk, or the like.

The input interface 223 is connected to the processing circuitry 225 and is configured to receive operations to input various types of instructions and information from the operator. More specifically, the input interface 223 is configured to convert the input operations received from the operator into electrical signals and to output the electrical signals to the processing circuitry 225. For example, the input interface 223 may be realized by using a trackball, a switch button, a mouse, a keyboard, a touch-pad on which an input operation can be performed by touching the operation surface thereof, a touch-screen in which a display screen and a touch-pad are integrally formed, a contactless input circuit using an optical sensor, an audio input circuit, and/or the like. In the present disclosure, the input interface 223 does not necessarily have to include one or more physical operational component parts such as a mouse, a keyboard, and/or the like. Examples of the input interface 23 include, for instance, electrical signal processing circuitry configured to receive an electrical signal corresponding to an input operation from an external input device provided separately from the apparatus and to output the electrical signal to a controlling circuit.

The display 224 is connected to the processing circuitry 225 and is configured to display various types of information and images. More specifically, the display 224 is configured to convert the information and data of the images sent thereto from the processing circuitry 225 into display-purpose electrical signals and to output the electrical signals. For example, the display 224 may be realized by using a liquid crystal monitor, a Cathode Ray Tube (CRT) monitor, a touch-panel, or the like.

The processing circuitry 225 is configured to control operations of the medical information processing apparatus 220 in accordance with the input operations received from the operator via tie input interface 223. For example, the processing circuitry 225 may be realized by using one or more processors.

A configuration of the medical image diagnosis system 200 according to the present embodiment has thus been explained. The medical image diagnosis system 200 according to the present embodiment structured as described above is configured to be able to perform a differential diagnosis process on various types f disease patterns, by using various types of images obtained by the MRI apparatus 100. Further, similarly to the first embodiment, the medical image diagnosis system 200 according to the present embodiment is configured to be able to efficiently perform the imaging processes required by the differential diagnosis process.

More specifically, similarly to the storage 12 explained in the first embodiment, the storage 222 included in the medical information processing apparatus 220 is configured to store therein a correspondence relationship among each of a plurality of disease patterns, a plurality of scans used for performing a differential diagnosis process on the disease pattern, and a plurality of regions used for performing a differential diagnosis process on the disease pattern.

Further, the processing circuitry 225 included in the medical information processing apparatus 220 includes an obtaining function 225a and an output controlling function 225b.

The obtaining function 225a is configured to perform the same processes as those performed by the obtaining function 16b explained in the first embodiment. It should be noted, however, that the obtaining function 225a in the present embodiment is configured to obtain first image data acquired from a first scan performed by the MRI apparatus 210 and second image data acquired from a second scan performed by the MRI apparatus 210, from the MRI apparatus 210 through the network 230 and via the NW interface 221.

The output controlling function 225b is configured to perform the same processes as those performed by the output controlling function 16c explained in the first embodiment. It should be noted, however, that the output controlling function 225b in the present embodiment is configured to transmit the imaging condition used for imaging the subject by performing the second scan, when it is not possible to perform the differential diagnosis process on the disease pattern on the basis of the first index value obtained by the obtaining function 225a, to the MRI apparatus 10 through the network 230 and via the NW interface 221.

In this situation, the output controlling function 225b may directly transmit the imaging condition to the medical image diagnosis apparatus. Alternatively, when imaging processes performed by medical image diagnosis apparatuses are managed by a medical examination appointment system at a hospital or the like, the output controlling function 225b may indirectly transmit the imaging condition to the medical image diagnosis apparatus by registering an additional order including the imaging condition into a queue of the medical examination appointment system.

Further, in the present embodiment, the input interface 223 and the display 224 are used in the same manner as the interface 10 and the display 11 are, respectively, in the first embodiment.

In the configuration illustrated in FIG. 6, the processing circuitry 225 may be realized by using one or more processors, for example. In that situation, the processing functions of the processing circuitry 225 are stored in the storage 222 in the form of computer-executable programs, for example. Further, the processing circuitry 225 realizes the functions corresponding to the programs by reading and executing the programs from the storage 222. In other words, the processing circuitry 225 that has read the programs has the processing functions illustrated in FIG. 6. In this situation, any of the processing circuitries may be structured by using a plurality of processors, so that the processing functions thereof are realized as a result of the processors executing the programs. Further, the processing functions of the processing circuitry 225 may be realized as being distributed to a plurality of processing circuitries or as being integrated together into a single piece of processing circuitry. Further, in the above description, the example is explained in which the single storage (the storage 222) is configured to store therein the programs corresponding to the processing functions; however, another arrangement is also acceptable in which a plurality of storages are provided in a distributed manner, so that any of the processing circuitries reads a corresponding one of the programs from a corresponding one of the individual storages.

By using the configuration described above, in the second embodiment also, the single session of medical examination is able to acquire all the pieces of image data required by the differential diagnosis process, similarly to the first embodiment. Further, it is possible to automatically execute the imaging process performed for the second time required by the differential diagnosis process. Consequently, according to the second embodiment, it is possible to efficiently perform the imaging processes required by the differential diagnosis process.

In the second embodiment above, the example is explained in which the medical image diagnosis apparatus is the MRI apparatus 210; however, possible embodiments are not limited to this example. For instance, the medical image diagnosis apparatus included in the medical image diagnosis system 200 may be an X-ray CT apparatus, a PET apparatus, an X-ray diagnosis apparatus, or the like.

Further, in the second embodiment above, the processing circuitry 225 may further include an extracting fun configured to perform the same processes as those performed by the extracting function lid explained in the modification example of the first embodiment. In that situation, the extracting function is configured to obtain either the text data or the electronic medical record data from either the VNA system or the electronic medical record system, through the network 230 and via the NW interface 221.

The term "processor" used in the explanations of the embodiments above denotes, for example, a Central Processing Unit (CPU), a Graphics Processing Unit (GPU), or a it such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). In this situation, instead of saving the programs in the storage, it is also acceptable to directly incorporate the programs in the circuits of the processors. In that situation, each of the processors realizes the functions thereof by reading and executing the corresponding one of the programs incorporated in the circuit thereof. Further, the processors in the present embodiments do not each necessarily have to be structured as a single circuit. It is also acceptable structure one processor by combining together a plurality of independent circuits so as to realize the functions thereof.

In this situation, the programs executed by the one or more processors are provided as being incorporated, in advance, in a Read-Only Memory (ROM), a storage, or the like. Alternatively, the programs may be provided as being recorded on a computer-readable storage medium such as a Compact Disk Read-Only Memory (CD-ROM), a Flexible Disk (FD), a Compact Disk Recordable (CD-R), a Digital Versatile Disk (DVD), or the like, in a file in such a format that is either installable or executable for the devices. Further, the programs may be stored in a computer connected to a network such as the Internet, so as to be provided or distributed as being downloaded via the network. For example, each of the programs is structured with a module including the functional units described above. In the actual hardware, as a result of a CPU reading and executing the programs from a storage medium such as a ROM, the modules are loaded into a main storage device so as to be generated in the main storage device.

According to at least one aspect of the embodiments described above, it is possible to efficiently perform the imaging processes required by the differential diagnosis process.

While certain embodiments have been described, these embodiments have been presented by way of example only, and are not intended to limit the scope the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus comprising:
   an imager configured to image a subject by performing a first scan;
   a storage configured to store therein information relating each of a plurality of disease patterns to a plurality of scans used for performing a differential diagnosis process on the disease pattern; and
   processing circuitry configured to obtain, on a basis of first image data acquired from the first scan, a disease pattern having applicability to the subject and a first index value indicating a degree of applicability of the disease pattern and configured to output information indicating the disease pattern to a display when it is possible to perform the differential diagnosis process on the disease pattern on the basis of the first index value and to output an imaging condition used for causing the imager to image the subject by performing a second scan different from the first scan on the basis of the information stored in the storage and the disease pattern having the applicability to the subject when it is not possible to perform the differential diagnosis process on the disease pattern on the basis of the first index value.

2. The medical image diagnosis apparatus according to claim 1, wherein, on a basis of second image data acquired from the second scan, the processing circuitry, again, obtains a disease pattern having applicability to the subject and a second index value indicating a degree of applicability of the disease pattern.

3. The medical image diagnosis apparatus according to claim 2, wherein the processing circuitry stores the first image data and the second image data into the storage as pieces of image data acquired from a same medical examination.

4. The medical image diagnosis apparatus according to claim 2, wherein the processing circuitry outputs the first image data, the second image data, and information indicating the disease pattern having the applicability to the subject, to the display.

5. The medical image diagnosis apparatus according to claim 1, wherein
   the imager includes a couch on which the subject is placed, and
   the processing circuitry causes the imager to perform the first scan and the second scan while the subject is kept on the couch.

6. The medical image diagnosis apparatus according to claim 1, wherein the processing circuitry further obtains a document describing both the disease pattern and the plurality of scans used for performing the differential diagnosis process on the disease pattern, generates the information relating each of the plurality of disease patterns to the plurality of scans by performing a text analysis on the document, and stores the generated information into the storage.

7. The medical image diagnosis apparatus according to claim 1, wherein
the storage further stores therein levels of priority of the scans, together with the information relating each of the plurality of disease patterns to the plurality of scans. and
the processing circuitry selects the second scan on the basis of the levels of priority.

8. The medical image diagnosis apparatus according to claim 1, wherein the imager images the subject by implementing magnetic resonance imaging.

9. The medical image diagnosis apparatus according to claim 1, wherein
the processing circuitry performs a process of dividing a brain region included in the first image data into a plurality of regions, and
the processing circuitry obtains the first index value in accordance with a result of the dividing process.

10. The medical image diagnosis apparatus according to claim 1, wherein
when it is not possible to perform the differential diagnosis process on the disease pattern on the basis of the first index value, the processing circuitry registers an additional order including the imaging condition used for imaging the subject by performing the second scan, into a medical examination appointment system, and p1 when an operator of the medical examination appointment system agrees to the additional order, the processing circuitry causes the imager to image the subject by performing the second scan.

11. A medical image diagnosis apparatus comprising:
an imager configured to image a subject by performing a first scan;
a storage configured to store therein information relating each of a plurality of disease patterns to a plurality of regions used for performing a differential diagnosis process on the disease pattern; and
processing circuitry configured to obtain, on a basis of a first region included in first image data acquired from the first scan, a disease pattern having applicability to the subject and configured to identify a second region different from the first region on a basis of the information stored in the storage and the disease pattern having the applicability to the subject and to output an imaging condition used for causing the imager to image the second region of the subject by performing a second scan.

12. The medical image diagnosis apparatus according to claim 11, wherein
together with the disease pattern having the applicability to the subject, the processing circuitry further obtains a first index value indicating a degree of applicability of the disease pattern, and
when it is not possible to perform the differential diagnosis process on the disease pattern on the basis of the first index value, the processing circuitry identifies the second region and outputs the imaging condition.

13. A medical image diagnosis apparatus comprising:
an imager configured to image a subject by performing a first scan;
a storage configured to store therein information relating each of a plurality of disease patterns to a plurality of scans used for perfoii ling a differential diagnosis process on the disease pattern; and
processing circuitry configured to obtain, on a basis of first image data acquired from the first scan, a disease pattern having applicability to the subject and a first index value indicating a degree of applicability of the disease pattern and configured to output information indicating the disease pattern to a display when it is possible to perform the differential diagnosis process on the disease pattern on the basis of the first index value and to output an imaging condition used for causing another medical image diagnosis apparatus to image the subject by performing a second scan different from the first scan on the basis of the information stored in the storage and the disease pattern having the applicability to the subject when it is not possible to perform the differential diagnosis process on the disease pattern on the basis of the first index value.

14. A medical image diagnosis system comprising a medical image diagnosis apparatus and a medical information processing apparatus, wherein
the medical image diagnosis apparatus includes: an imager configured to image a subject by performing a first scan, and
the medical information processing apparatus includes:
a storage configured to store therein information relating each of a plurality of disease patterns to a plurality of scans used for performing a differential diagnosis process on the disease pattern; and
processing circuitry configured to obtain, on a basis of first image data acquired from the first scan, a disease pattern having applicability to the subject and a first index value indicating a degree of applicability of the disease pattern and configured to output information indicating the disease pattern to a display when it is possible to perforin the differential diagnosis process on the disease pattern on the basis of the first index value and to output an imaging condition used for causing the medical image diagnosis apparatus to image the subject by performing a second scan different from the first scan on the basis of the information stored in the storage and the disease pattern having the applicability to the subject when it is not possible to perform the differential diagnosis process on the disease pattern on the basis of the first index value.

* * * * *